United States Patent
Bejjani et al.

[11] Patent Number: 5,090,042
[45] Date of Patent: Feb. 18, 1992

[54] VIDEOFLUOROSCOPY SYSTEM FOR IN VIVO MOTION ANALYSIS

[76] Inventors: Fadi J. Bejjani, 35 W. 4 St., New York; Ricky Lockett, 100 E. 92 St. 5J, Brooklyn; Lazaros Pavlidis, 93-21 71st Dr., Forest Hills, all of N.Y.

[21] Appl. No.: 632,919

[22] Filed: Dec. 24, 1990

[51] Int. Cl.[5] .............................................. H05G 1/64
[52] U.S. Cl. ........................................ 378/99; 358/111
[58] Field of Search ............................ 358/111; 378/99

[56] References Cited

U.S. PATENT DOCUMENTS 4,387,392  6/1983  Grattoni et al. ................... 358/111

Primary Examiner—Craig E. Church
Attorney, Agent, or Firm—Arthur L. Plevy

[57] ABSTRACT

A videofluoroscopy system for use in vivo, real-time, motion analysis includes a fluoroscopy system for producing a series of x-ray images of a subject, a video recorder for recording the x-ray images as video frame images, a video playback unit for providing a playback output of individual video image frames one at a time, a frame grabber connected to a display monitor for converting each image frame into graphics data and displaying a selected viewing area thereof on the monitor, a marking device for marking selected points within the viewing area of each image frame, and a computer processor for controlling the frame grabber, display, and marking device in order to define the viewing area, detect X-Y coordinates for the selected points, and store the coordinates of the marking points as motion data. The frame grabber is implemented as a module connected to the computer processor which automatically operates the video playback unit and converts the image frames one frame at a time to digital graphics data. The motion data can be retrieved for display superimposed with the video images in real-time motion, for motion simulation, and/or for motion analysis. The use of in vivo fluoroscopic images is particularly suited for medical analysis of internal bodily structures and conditions.

20 Claims, 2 Drawing Sheets

VIDEOFLUOROSCOPY SYSTEM FOR IN VIVO MOTION ANALYSIS

FIELD OF INVENTION

The present invention relates to a system and method for in vivo motion analysis, and particularly, to one which derives internal motion data from fluoroscopy images of a human subject in video form.

BACKGROUND OF INVENTION

Human motion analysis systems, also known as performance analysis systems, have found increasing use in evaluating the motions of the human body. Such systems have been of assistance in analyzing athletic performance and for biomechanical and medical uses. Conventional motion analysis techniques usually involve taking video recordings of the motions of a subject, and deriving digital data representing the motions by recording the positions of highlighted skin markers or by manual marking of certain points of the body. The digital data are then analyzed by visual discrimination, comparison to the motions of other subjects or standards, and/or by computational analysis of selected motion factors.

However, motion analysis systems have been limited to the analysis of external points on the body and relatively superficial factors, such as speed, gait, angular positions of body parts, etc. They do not take into account the internal motion dynamics of individual subjects, which may be affected by such factors as physical anatomy, skeletal structure, muscle or organ condition, and other internal features.

Radiography has long been used in medical practice to evaluate internal structures, particularly bone structures and, to a lesser extent, organs and soft tissues. X-ray photographs can reveal bone fractures, dislocations, deformities, and degenerative conditions. One important medical area is analysis of the spine and joints and their response under certain stresses, positions, and/or motions. In order to compare changes to the area under study, conventional radiography utilizes visual analysis of x-ray photographs of the subject area in different positions. However, static photographs can provide only a limited amount of information and requires the medical practitioner to interpolate between photographs and to rely on memory and visual discrimination.

Dynamic evaluation of the motion of internal structures is facilitated by techniques developed in fluoroscopy and radiography. Fluoroscopy can provide an x-ray image display of a subject area undergoing motion for dynamic evaluation. Videofluoroscopy involves recording the fluoroscopic images in video form for further review. While these techniques do provide excellent tools for dynamic evaluation of motion, they have many problems and disadvantages which limit their effectiveness. Videofluoroscopy is recorded in real-time, so that high speed motions or rapid changes result in distorted or blurred images. The viewing frame is generally small, compared to standard radiographs, and is fixed once a subject in motion is recorded. Thus, detailed discrimination and accurate measurement of different areas within the viewing frame is made difficult. Repeated recordings of a subject can often be required, thereby increasing exposures to radiation. Also, dynamic evaluation in conventional fluoroscopy or cineradiography involves visual inspection and discrimination, which limits the amount of information that can be derived by the medical practitioner.

SUMMARY OF INVENTION

It is therefore a principal object of the invention to provide a system and method for in vivo, real time, motion analysis. It is a specific object to provide such a system which is capable of recording clear internal images of a range of human motions and functions of low to high speed and deriving internal data therefrom. Also, it is intended that the invention allow the viewing frame for motion analysis to be adjusted for zooming in on different areas of the overall recording frame, so that particular areas can be evaluated and the amount of motion data derived from the recorded images can be increased. It is particularly desired that such a system be usable for real-time medical analysis, for example, of spinal motion, the stability of spinal segments, soft tissue motion, diaphragmatic motion, the swallowing mechanism, as well as the motion of body joints and limbs.

In accordance with the invention, a videofluoroscopy system for in vivo, real time, motion analysis comprises:

(a) fluoroscope means for irradiating a subject in motion and producing a series of x-ray images of the subject;

(b) video recording means for recording the x-ray images as video image frames on a video recording medium;

(c) video playback means for providing a playback output of the video image frames recorded on the video recording medium;

(d) frame grabbing means coupled to said video playback means for receiving a playback of video image frames from said video recording medium and providing an output of individual image frames one frame at a time;

(e) display means coupled to said frame grabbing means for displaying a viewing area of each individual image frame provided at a time as an output from said frame grabbing means;

(f) marking means for marking selected points within the viewing area of each individual image frame displayed by said display means; and (g) computer processor means coupled to at least said frame grabbing means, display means, and marking means for defining X-Y dimensions for the viewing area displayed by said display means, for detecting X-Y coordinates for each of the selected marking points within the defined viewing area, and for storing the X-Y coordinates of the selected marking points for each image frame thus marked as motion data.

The invention encompasses the related method of video recording and playback of in vivo fluoroscopic images and frame-by-frame marking of selected points of such images as in vivo motion data. In the preferred embodiment of the system, the frame grabber is implemented as an interface module connected to the computer processor which receives video image frames from the video playback device and converts them to individual image frames in the form of digital graphics data stored in a buffer. The computer processor operates the frame grabber and video playback device under program control to grab and convert one image frame at a time. Program control of the converted digital graphics data for display allows the user to selectively define the viewing area for any part or the whole of the entire image frame, including magnifying or reducing (zooming) the display of an area of interest. Marking is accomplished with a cursor or mouse pointer or other pointing device. The coordinates of the marking points are stored together with the definition of the viewing area for the series of image frames constituting the recording of the subject's motion, and can later be retrieved for display in real-time motion, review, and/or analysis. Different sets of viewing areas and motion data can be defined and derived for multiple parts or segments of the overall image frame for a fluoroscopic recording, thereby avoiding the need for multiple recordings and excessive radiation exposures of the subject. The locations on the video recording medium of the image frames which are converted may also be stored with the motion data, so that the marking points may be displayed superimposed on the video images of the subject. Conventional or customized motion analysis programs can be selectively applied to the motion data captured by the system.

BRIEF DESCRIPTION OF DRAWINGS

The above objects and further features and advantages of the invention are described in detail below in conjunction with the drawings, of which.

DETAILED DESCRIPTION OF PREFERRED EMBODIMENTS

Figure 1:
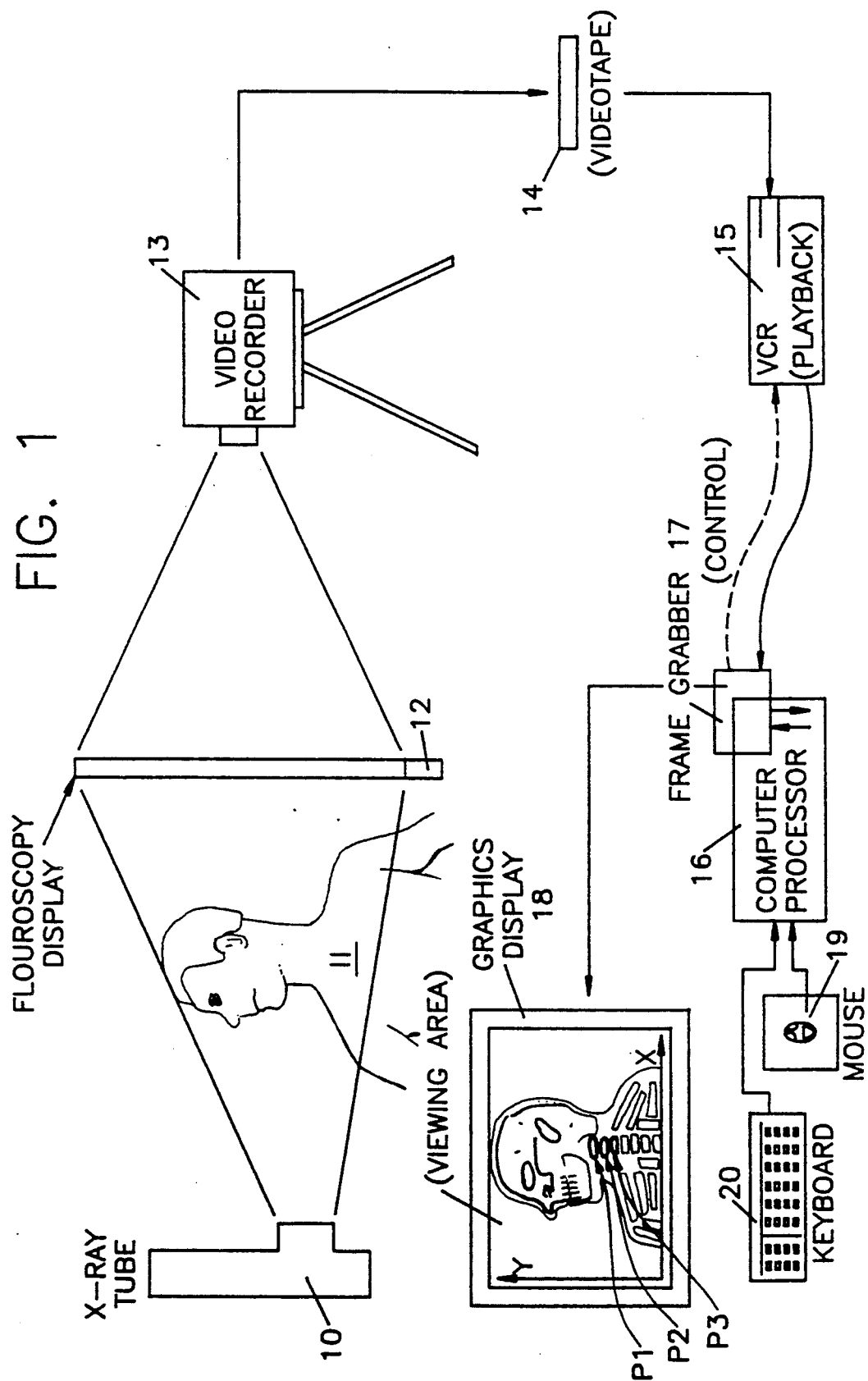
FIG. 1 is a schematic diagram of a videofluoroscopy system for in vivo motion analysis in accordance with the invention.

Referring to FIG. 1, a videofluoroscopy system for in vivo motion analysis in accordance with the invention includes an x-ray table 12 from which a scanning x-ray gun 10 irradiates a subject 11 with x-rays in order to provide a series of real-time x-ray images of the subject 11 which is captured by a video recording camera 13 on a videotape 14. The subject 11 can perform a motion while on the table 12, such as moving the head, neck, and/or shoulders, or perform various bodily functions, such as swallowing. The video recording camera 13 captures the corresponding x-ray images of the internal bone and tissue structure in motion. The camera 13 may also be used to record a series of still x-ray images. Videofluoroscopy systems suitable for use as described above are commercially available, for example, the Model TEC-5350 sold by Teknomed USA, of Long Island, N.Y., the Vector 1050 sold by Picker Corp., of Cleveland, Ohio, the Pantoskop-5 or Sireskop-5 sold by Siemens Corp., of Solna, Sweden, or the Prestalix units sold by GE Corp., of Fairfield, Conn.

When the x-ray images of the subject's motion have been recorded, the videotape is inserted into a VCR unit 15 which has a playback function. A computer processor system 16 is used to control the playback, display, and conversion of the recorded x-ray images into motion data, which can then be analyzed visually or by motion analysis programs.

A frame grabber module 17 is connected to the computer processor 16 and operates to grab one video image frame at a time played back from the videotape by the VCR unit 15. The frame grabber converts the image on the video image frame to digital graphics data which are stored in a buffer. The converted graphics image frame stored in the buffer is output for display on a graphics image display monitor 18.

A user of the system can now mark certain points on each image frame displayed on the display 18 for analysis as motion data. The user defines beforehand the viewing area of the display 18 in terms of its X and Y dimensions relative to the overall frame area of the recorded images. For example, the overall frame area of the recorded images may encompass the entire height and width of the subject, whereas the viewing frame may be defined as only the portion framing the subject's head, neck, and shoulders. Alternatively, the overall frame area may encompass the same subject matter as the converted image frame, but the viewing area may be defined as a magnification or reduction of the recorded frame area. Definition of the viewing area dimensions allows the proper calculation of the coordinates of the points to be marked relative to the viewing area and to the overall frame area.

Once the X-Y dimensions of the viewing area have been defined, the coordinates of any points that are marked can be determined relative to the reference viewing area. The points, e.g. points P1, P2, P3 shown in FIG. 1, are selected to highlight the internal elements of interest for motion analysis. They may be points of bone structures, joints, soft tissue, or other internal features. The points are marked by moving a pointing device, such as a mouse 19 which is connected to the processor 16, until a cursor on the display is in registration with the point of the displayed image to be marked. Other pointing devices, such as a light pen, touch screen, etc., may be used. Currently, a mouse provides the requisite degree of X-Y resolution for marking the coordinates of typical x-ray images. A keyboard 20 is also connected to the computer processor 16 for entering keyed input to the system.

When the points of interest in the viewing area have been marked, the user presses a key command to store the coordinates of the marked points. This procedure is repeated for each frame grabbed by the frame grabber 17 from the series of recorded video image frames played back from the videotape 14. The marked coordinates for the points of the thus processed frames and the definition of the viewing area are stored by the processor 16 in memory as motion data.

Figure 2:
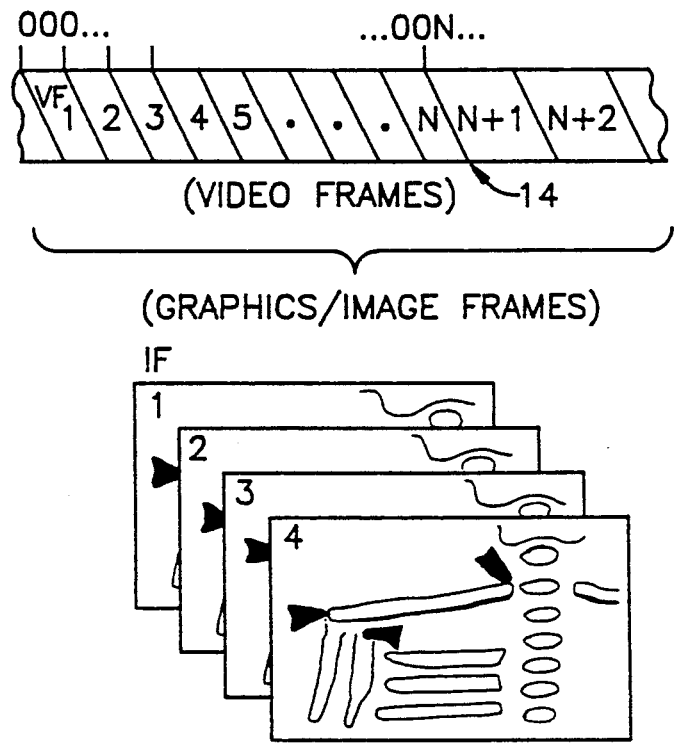
FIG. 2 is a diagram of the conversion of video image frames to graphics image frames and the marking of selected points as motion data thereon.

FIG. 2 depicts the relationship between the video image frames recorded on videotape 14 and the converted graphics image frames displayed on the display 18 for a user of the system. As is well known in conventional videotape recording, a series of videotape image frames VF are recorded on the videotape 14. The frame grabber 16 may grab each video image frame in series for conversion to graphics image frames IF. In a typical application, video image frames are recorded at the rate of 30 frames/second for a performance of a motion by the subject which may be of a duration of 3 to 10 seconds. The frame grabber converts the 100 to 300 video image frames one frame at a time to each corresponding graphics image frame which is stored in the buffer of the frame grabber and displayed on the display 18 for marking.

As each graphics image frame IF is marked, the coordinates of the marked points are stored, and the next video image frame VF is converted and stored in the buffer. The buffer capacity may typically be 250K to 500K or more for bit-mapped display of an image frame. If the subject's motion is performed at a relatively slow speed, it may be desirable to convert and mark only every nth video image frame as a graphics image frame. The selection of the frame conversion ratio is entered beforehand in the processor 16 and used to control the function of the frame grabber. The location of the first video frame in the sequence, designated 000 in FIG. 2, is also stored with the motion data, so that the marked points data can later be played back superimposed on the video images in a proper time registration. Alternatively, the graphics image data may be downloaded from the buffer into memory for storage of the entire converted graphics image. However, because of the large memory requirement, it is currently more efficient to display the marked points superimposed on the played-back video images, rather than storing the converted graphics images.

Commercially available VCR units and computer equipment (display, keyboard, processor, mouse) are suitable for use in the invention. The computer processor may be the standard personal computer or workstation configuration with graphics capability. Frame grabbers suitable for use in this system are available commercially, for example, the Spectrum NTSC, sold by Redlake Corporation, of Morgan Hill, Calif. Such commercial units execute the function of converting an input video image frame to bit-mapped graphics data and displaying the graphics image on the associated display. Frame grabbers can also include image processing functions which improve image resolution and clarity, color, hue, contrast, brightness, and saturation. The frame grabber provides an advantage over the freeze-frame function of conventional VCR units, in that the frame grabber stores the retrieved image digitally, such that it can be processed, manipulated, and restored over an extended period of time, whereas operation of the VCR unit in the freeze-frame playback mode would cause damage to the videotape.

The conventional frame grabber units are limited in that they require the user to control the associated functions of the processor 16 and the VCR unit 15 manually for each image frame to be converted. In accordance with a further aspect of the invention, a frame grabber can be designed as a fully self-contained module which executes all of the necessary functions automatically by issuing the requisite control commands to the processor 16, VCR unit 15, and display 18.

Figure 3:
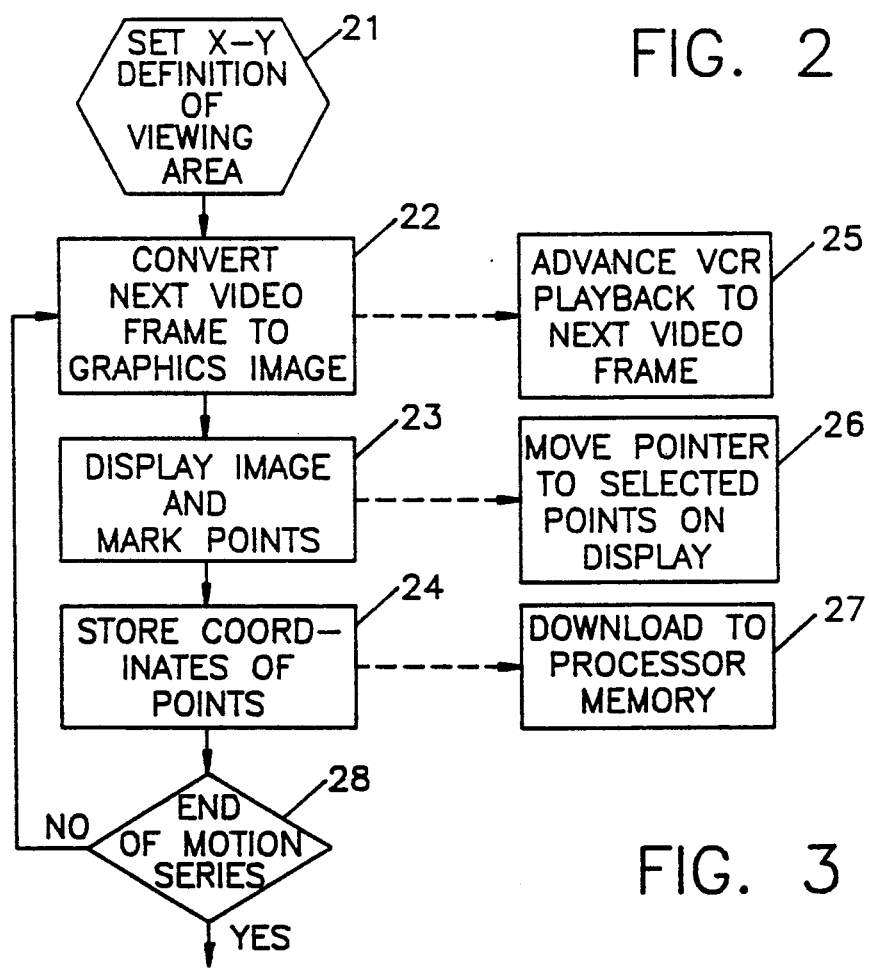
FIG. 3 is a diagram of the elements of the frame grabber control for the system of the invention.

In FIG. 3, an example of a preferred frame grabber for automatic image conversion control is shown in block diagram form. The definition of the X-Y dimensions and/or location of the viewing area relative to the overall image frame is first established at block 21. The frame grabber then executes sequential processing of each image frame by conversion to the graphics image frame, at block 22, displaying the graphics image on the display for marking of the points, at block 23, then storing the coordinates of the marked points, at block 24. The frame grabber module 17 can be designed to provide the necessary control commands to the VCR unit 15 to advance playback to the next video image frame to be converted, as shown at block 25. It may also be designed as an interface between the position signals of the mouse 19 and display of the mouse pointer on the graphics image, as indicated at block 26. The frame grabber module may also perform the downloading of the graphics image data stored in the buffer to the processor memory in the mode in which the graphics image is to be stored, as indicated at block 27.

The arrows indicated in dashed lines in FIG. 3 represent control signals issued from the frame grabber to the other components of the system, i.e. the VCR unit 15, the display 18, and the processor 16. When the end of the motion series is reached, the frame grabber control sequence is exited, as indicated at block 28. These functions of the frame grabber may be implemented by storing the frame grabber program in ROM and using the stored program to control a command signal switch array, buffer, image processor, and display driver hardwired on a card to be inserted in an expansion slot of the processor 16. Alternatively, the frame grabber program may be a software program executed by the processor 16. Two or more frame grabbers may also be operated in parallel to convert and store motion data on different portions or segments of the overall image frame of a recorded motion sequence.

The stored motion data can later be retrieved from memory for viewing and analysis. The marked points constituting the motion data can be displayed superimposed on played-back video images or with stored graphics images, as mentioned above. The database of marked points may also be imported for analysis by motion analysis programs. Computerized analysis of motion data is a widely used technique in human motion analysis. Programs which analyze the external movements of joints and limbs of the human body can similarly be used for analysis of internal points marked in the fluoroscopic images. Human performance analysis programs such as ARIEL and VICOM are widely used in biomechanics research centers and sports training centers. Customized programs may be designed to take advantage of the greater level of information about internal organs, soft tissue, and structural features available from the fluoroscopic images used in the present invention.

The combined use of videofluoroscopy images, the frame grabber function, and computerized control as disclosed above results in a new system having the capability to record, convert, and analyze in vivo fluoroscopic images for motion analysis. The system has novel applications in a wide range of medical areas, such as cervical spine motion. The stability and movement of spinal segments can be analyzed to discriminate between normal and pathological relationships of the vertebrae. Internal conditions, such as the instabilities of spondylolisthesis, congenital absence of a pedicle, osteo-arthritis, rheumatoid arthritis, diaphragmatic movements, rheumatoid subluxations, laminectomies, shoulder dysfunctions, etc., can be detected. An accurate evaluation can be made of the stabilizing effects of various orthopedic components, procedures, and prosthetics both before and after application. The progress or motion of internal markers can also be recorded and evaluated, for example, the progress of a contrast medium of radio-opaque paste through the peristaltic vessels of the body. These normally non-visible internal features and structures can thus be analyzed and measured in real time. Once the initial fluoroscopic sequence is recorded, the recording can be converted and analyzed for different parts or multiple segments of the body or with different magnifications or image processing techniques to optimize the capture of information, without the need for repeated radiological exposure of the subject. The motion data may later be digitally enhanced or manipulated in simulations of different motion patterns.

The specific embodiments of the invention described herein are intended to be illustrative only, and many other variations and modifications may be made thereto in accordance with the principles of the invention. All such embodiments and variations and modifications thereof are considered to be within the scope of the invention, as defined in the following claims.

We claim:

1. A videofluoroscopy system for in vivo motion analysis comprising:
   (a) fluoroscope means for irradiating a subject in motion and producing a series of x-ray images of the subject;
   (b) video recording means for recording the x-ray images as video image frames on a video recording medium;
   (c) video playback means for providing a playback output of the video image frames recorded on the video recording medium;
   (d) frame grabbing means coupled to said video playback means for receiving a playback of video image frames from said video recording medium and providing an output of individual image frames one frame at a time;
   (e) display means coupled to said frame grabbing means for displaying a viewing area of each individual image frame provided at a time as an output from said frame grabbing means;
   (f) marking means for marking selected points within the viewing area of each individual image frame displayed by said display means; and
   (g) computer processor means coupled to at least said frame grabbing means, display means, and said marking means for defining X-Y dimensions for the viewing area displayed by said display means, for detecting X-Y coordinates for each of the selected marking points within the defined viewing area, and for storing the X-Y coordinates of the selected marking points for each image frame thus marked as motion data.

2. A videofluoroscopy system according to claim 1, wherein said fluoroscopy means includes an x-ray table and video recording camera.

3. A videofluoroscopy system according to claim 1 wherein said frame grabbing means includes converter means for converting the received video image frame into graphics image data, and a buffer for storing the graphics image data.

4. A videofluoroscopy system according to claim 1, wherein said frame grabbing means includes control means for automatically controlling said video playback means for providing a playback output of each video image frame in sequence.

5. A videofluoroscopy system according to claim 4, wherein said frame grabbing means includes control means for automatically controlling said video playback means for providing a playback output of every nth video image frame of the video image frames recorded on the videotape, wherein n is a positive integer greater than 1.

6. A videofluoroscopy system according to claim 1, wherein said frame grabbing means is formed as a self-contained module which is coupled to said computer processor means.

7. A videofluoroscopy system according to claim 1, wherein said marking means is a device connected to said computer processor means for controlling the position of a marking element displayed on said display means.

8. A videofluoroscopy system according to claim 3, wherein said frame grabbing means includes display control means for controlling the display of any selected portion of the video image frame within the viewing area on said display means in response to user input to said computer processor means.

9. A videofluoroscopy system according to claim 1, wherein said computer processor means includes an associated memory for storing the motion data.

10. A videofluoroscopy system according to claim 3, wherein said frame grabbing means includes downloading means for downloading the graphics image data from said buffer to a memory associated with said computer processor means.

11. A videofluoroscopy method for performing in vivo motion analysis comprising the steps of:
    (a) irradiating a subject in motion and producing a series of x-ray images of the subject;
    (b) recording the series of x-ray images as video image frames on a video recording medium;
    (c) providing a playback output of the video image frames recorded on the video recording medium;
    (d) receiving a playback of video image frames from the video recording medium and providing an output of individual image frames one frame at a time;
    (e) displaying within a viewing area each individual image frame provided at a time;
    (f) marking selected points within the viewing area of each individual image frame displayed; and
    (g) defining X-Y dimensions for the viewing area displayed, detecting X-Y coordinates for each of the selected marking points within the defined viewing area, and storing the X-Y coordinates of the selected marking points for each image frame thus marked as motion data.

12. A videofluoroscopy method according to claim 11, wherein said frame receiving step includes converting the received video image frame into graphics image data, and storing the graphics image data in a buffer.

13. A videofluoroscopy method according to claim 11, further comprising the step of retrieving said motion data and displaying the marked points in a motion sequence on a display.

14. A videofluoroscopy method according to claim 11, further comprising the step of displaying the marked points superimposed with the recorded image frames in a motion sequence on a display.

15. A videofluoroscopy method according to claim 11, wherein said displaying step includes magnifying or reducing (zooming) the display of an area of the overall image frame.

16. A videofluoroscopy method according to claim 11, wherein said marking and defining steps include marking different sets of defined viewing areas and storing motion data for multiple parts or segments of the overall image frame for a recorded motion sequence.

17. A videofluoroscopy method according to claim 11, further comprising the step of analyzing the motion data computationally using a motion analysis program.

18. A videofluoroscopy method according to claim 11, wherein the subject is a human body, and further comprising the step of analyzing the motion data for medical data.

19. A videofluoroscopy method according to claim 11, further comprising the step of retrieving said motion data and manipulating the marked points to provide a simulation of a motion sequence on a display.

20. A videofluoroscopy method according to claim 11, wherein said frame receiving step includes automatically performing the playback of the video image frames by operating a videocassette recorder (VCR) unit under control of a frame grabber module connected to a computer processor.

* * * * *